United States Patent
Fukui et al.

(10) Patent No.: US 10,598,601 B2
(45) Date of Patent: Mar. 24, 2020

(54) GAS CONCENTRATION MEASURING DEVICE

(71) Applicants: Yanmar Co., Ltd., Osaka-shi, Osaka-fu (JP); Fuji Electric Co., Ltd., Kawasaki-shi, Kanagawa-ken (JP)

(72) Inventors: Yoshinori Fukui, Osaka (JP); Ryota Kobayashi, Osaka (JP); Tetsuya Yokoyama, Osaka (JP); Tsuyoshi Inoue, Osaka (JP); Yusuke Oda, Osaka (JP); Michiyasu Okada, Kawasaki (JP); Kozo Akao, Kawasaki (JP); Ryouichi Higashi, Kawasaki (JP)

(73) Assignees: YANMAR CO., LTD., Osaka (JP); FUJI ELECTRIC CO., LTD., Kawasaki (JP)

( * ) Notice: Subject to any disclaimer, the term of this patent is extended or adjusted under 35 U.S.C. 154(b) by 0 days.

(21) Appl. No.: 16/087,461

(22) PCT Filed: Mar. 6, 2017

(86) PCT No.: PCT/JP2017/008798
§ 371 (c)(1),
(2) Date: Sep. 21, 2018

(87) PCT Pub. No.: WO2017/163841
PCT Pub. Date: Sep. 28, 2017

(65) Prior Publication Data
US 2019/0094148 A1      Mar. 28, 2019

(30) Foreign Application Priority Data

Mar. 24, 2016 (JP) ................................. 2016-060038

(51) Int. Cl.
*G01N 21/85* (2006.01)
*G01N 21/15* (2006.01)
(Continued)

(52) U.S. Cl.
CPC ............. *G01N 21/85* (2013.01); *G01N 21/03* (2013.01); *G01N 21/15* (2013.01);
(Continued)

(58) Field of Classification Search
CPC ........ G01N 21/85; G01N 21/03; G01N 21/15; G01N 21/3504; G01N 2021/151; G01N 2021/8578
See application file for complete search history.

(56) References Cited

U.S. PATENT DOCUMENTS

| 5,374,399 A | 12/1994 | Tsukamoto et al. |
| 2008/0011049 A1* | 1/2008 | Dani ...................... G01N 21/15 73/23.2 |

FOREIGN PATENT DOCUMENTS

| CN | 102062726 A | 5/2011 |
| DE | 10309604 A1 | 9/2004 |

(Continued)

OTHER PUBLICATIONS

International Search Report dated Apr. 11, 2017 issued in corresponding PCT Application PCT/JP2017/008798.
(Continued)

*Primary Examiner* — Jamil Ahmed
(74) *Attorney, Agent, or Firm* — Norton Rose Fulbright US LLP (57) ABSTRACT

A gas concentration measuring device including a light emitter and a light receiver which are disposed so as to be opposed to each other with a hollow tube-like measurement pipe interposed therebetween. The device is configured to measure concentration of target gas passing through the measurement pipe using light applied from the light emitter, transmitted through the inside of the measurement pipe, and received by the light receiver. Purge gas guide pipes through which purge gas is introduced into optical systems of the
(Continued)

light emitter and the light receiver are connected to a side wall of the measurement pipe. The measurement pipe includes a gas entrance portion having a tapered shape widening from a gas supply port toward a downstream side thereof.

18 Claims, 4 Drawing Sheets

(51) Int. Cl.
  *G01N 21/3504* (2014.01)
  *G01N 21/03* (2006.01)
(52) U.S. Cl.
  CPC ... *G01N 21/3504* (2013.01); *G01N 2021/151* (2013.01); *G01N 2021/8578* (2013.01)

(56) References Cited

FOREIGN PATENT DOCUMENTS

| | | |
|---|---|---|
| JP | 1988-111654 U | 7/1988 |
| JP | 03-154852 A | 7/1991 |
| JP | 1993-003988 U | 1/1993 |
| JP | 2001-083075 A | 3/2001 |
| JP | 2007-285721 A | 11/2007 |
| JP | 5606056 B2 | 9/2014 |

OTHER PUBLICATIONS

European Search Report dated Dec. 21, 2018 issued in corresponding European Application No. 17769886.

\* cited by examiner

GAS CONCENTRATION MEASURING DEVICE

CROSS REFERENCES TO RELATED APPLICATIONS

This application is a national stage application pursuant to 35 U.S.C. § 371 of International Application No. PCT/JP2017/008798, filed on Mar. 6, 2017 which claims priority of under 35 U.S.C. § 119 to Japanese Patent Application No. 2016-060038 filed on Mar. 24, 2016, the disclosures of which are hereby incorporated by reference in their entireties.

TECHNICAL FIELD

The present invention relates to a gas concentration measuring device configured to measure concentration of one or more components of gas flowing through a pipe. In particular, the invention relates to a gas concentration measuring device configured to apply light for measurement.

BACKGROUND ART

Conventionally, gas concentration measuring devices utilizing light have been used to measure various types of gas components of exhaust gas from a combustion system such as an internal combustion engine and an incinerator, and gas components of fuel gas to a gas system such as a gas engine and a fuel cell. Examples of known measurement methods using such a light-applying gas concentration measuring device include: Fourier-transform infrared spectroscopy (FTIR), which is a technique utilizing distribution of intensity of interfered infrared light; and tunable diode laser absorption spectroscopy (TDLAS), which is a technique utilizing absorption of applied laser light.

A TDLAS gas concentration measuring device is configured to measure concentration of a gas species of interest for measurement ("target gas") by applying laser light having a wavelength corresponding to the absorption spectrum of the target gas and measuring the amount of attenuation of laser light transmitted through the gas (see Patent Literature 1 (PTL 1)). The TDLAS gas concentration measuring device is configured to eject purge gas such as instrument air and nitrogen gas to its measurement-purpose optical systems to prevent contamination of and condensation on the optical systems.

CITATION LIST

Patent Literature

PTL 1: Japanese Patent No. 5606056

SUMMARY OF INVENTION

Technical Problem

In TDLAS technique, the concentration of the target gas is measured based on the following Equation (1), which is based on Lambert-Beer law. That is, in the gas concentration measurement method according to TDLAS, the optical path length of laser light passing through a measuring object ("transmitting optical path length") as a parameter. For precise analysis of gas concentration, it is preferable that the optical path length of laser light passing through sample gas (area) does not vary. For this purpose, it is necessary to make a measurement width constant, which is the width of area in which the target gas flows.

$$I1 = I0 \times \exp(-\varepsilon \times N \times L) \quad \text{Equation (1)}$$

(where $I0$ represents intensity of laser light before passing through the object; $I1$ represents intensity of laser light after passing through object; $\varepsilon$ represents molar absorption coefficient; $N$ represents molar concentration of the object; and $L$ represents the transmitting optical path length.)

In this regard, however, in a known gas concentration measuring device in which a light emitter and a light receiver are provided so that a pipe (measurement cell) through which target gas flows is interposed between the light emitter and the light receiver, sample gas flowing through the pipe enters gas concentration measuring instruments of the device. To prevent contamination of or damage to optical systems of the light emitter and the light receiver of the gas concentration measuring device, guide pipes for introducing purge gas are provided, and purge gas is ejected from the guide pipes to prevent the entry of the sample gas. However, if the flow rate of the purge gas is not appropriate, the above-mentioned measurement width (transmitting optical path length $L$) becomes unstable, which reduces reliability of measured values.

Solution to Problem

An object of the present invention is to provide a gas concentration measuring device improved in view of the above-described circumstances.

In an aspect of the present invention, a gas concentration measuring device includes a light emitter and a light receiver which are disposed so as to be opposed to each other with a hollow tube-like measurement pipe interposed therebetween, and the device is configured to measure concentration of target gas passing through the measurement pipe using light applied from the light emitter, transmitted through an inside of the measurement pipe, and received by the light receiver. Purge gas guide pipes through which purge gas is introduced into optical systems of the light emitter and the light receiver are connected to a side wall of the measurement pipe, and are provided so as to be opposed to each other and to be orthogonal to a flow direction of the target gas; and the measurement pipe includes a gas entrance portion having a tapered shape widening from a gas supply port toward a downstream side in the flow direction of the target gas.

The gas concentration measuring device may be arranged such that the measurement pipe includes a gas exit portion provided downstream of the measurement portion, and the gas exit portion has a tapered shape narrowing toward a gas discharge port of a downstream end portion of the measurement pipe in the flow direction of the target gas.

Furthermore, the gas concentration measuring device may be arranged such that an exhaust gas outlet may be provided close to a main passage or close to a bypass passage.

Furthermore, the gas concentration measuring device may be arranged such that a flow rate of purge gas supplied to the purge gas guide pipes is calculated based on: a ratio of a cross-sectional area of the measurement portion functioning as a longer-diameter portion to a cross-sectional area of a gas inlet port functioning as a shorter-diameter portion; and a flow rate of gas entering the measurement pipe.

Furthermore, the gas concentration measuring device may be arranged such that the device is configured to detect a change of the flow rate of gas entering the measurement pipe, and to adjust the flow rate of purge gas depending on the detected change.

Advantageous Effects of Invention

According to an embodiment of the present invention, entry of sample gas into connecting portions between the purge gas guide pipes and the measurement pipe can be suppressed or reduced in the measurement pipe. Therefore, the optical path length of laser light applied to the sample gas in the measurement pipe can be maintained constant, to improve the reliability of measured gas concentration values. In addition, it is possible to suppress or reduce the flow rate of purge gas supplied to the purge gas guide pipes. This can lead to not only downsizing of devices for supplying purge gas but also reduction of power and/or fuel cost to supply purge gas.

Furthermore, according to an embodiment of the present invention, the larger the ratio of the cross-sectional area of the longer-diameter portion of the measurement pipe to the cross-sectional area of the shorter-diameter portion of the measurement pipe, the better the entry of the sample gas into the purge gas guide pipes is suppressed or reduced. Thus, the flow rate of purge gas can be calculated easily and can be properly set depending on the flow rate of the sample gas.

DESCRIPTION OF EMBODIMENTS

Figure 1:
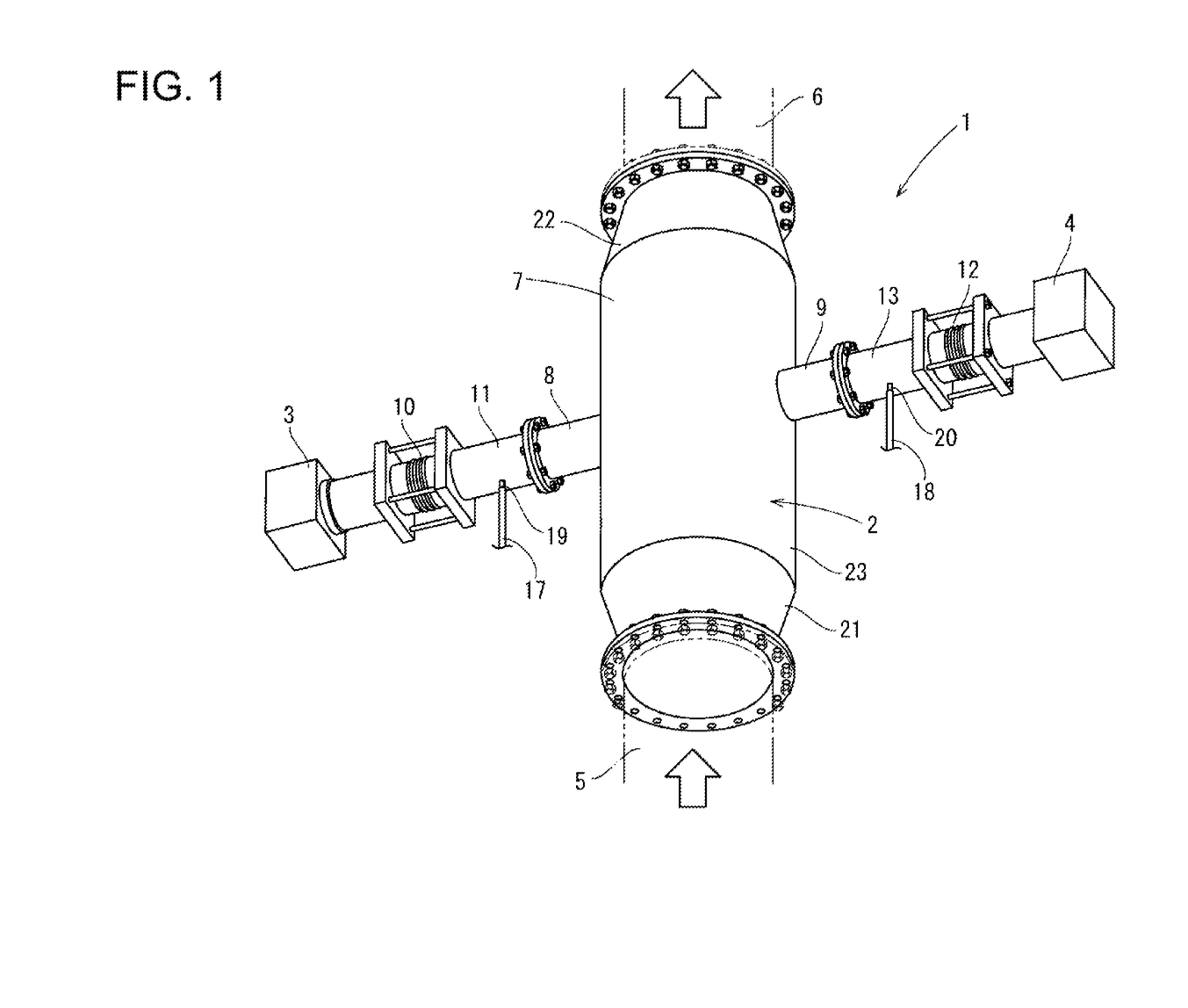
FIG. 1 A perspective view illustrating a structure of a gas concentration measuring device, including a measurement pipe.

The following will describe a gas concentration measuring device of an embodiment of the present invention, with reference to drawings. FIG. 1 is a schematic perspective view illustrating a structure of the gas concentration measuring device of the present embodiment.

Figure 2:
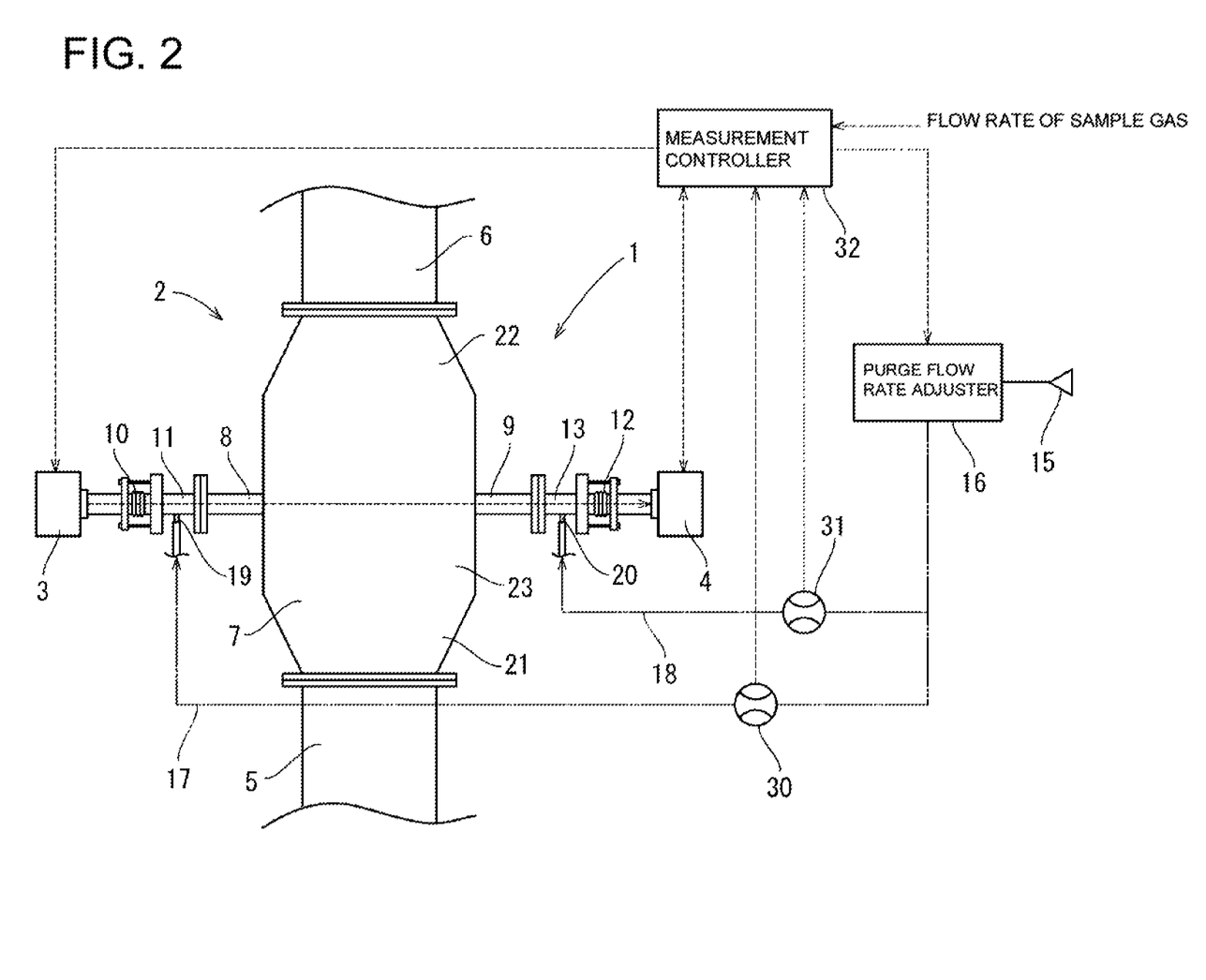
FIG. 2 A schematic diagram illustrating a system structure of the gas concentration measuring device.
Figure 3:
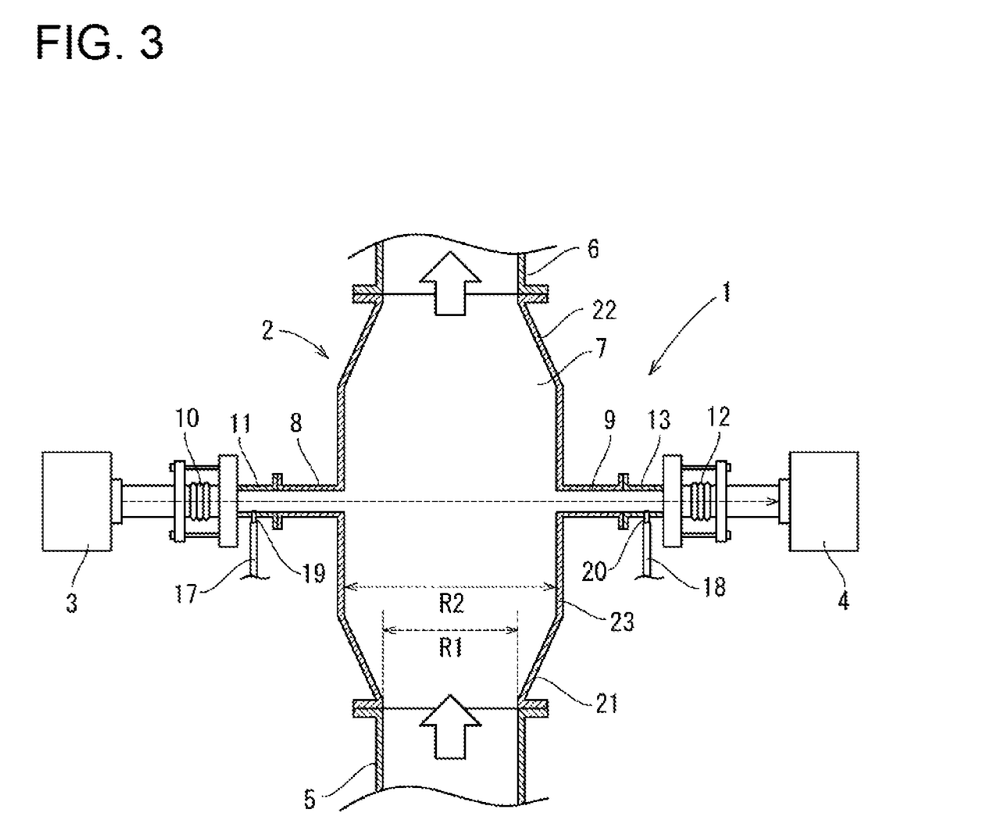
FIG. 3 A cross-sectional view of the gas concentration measuring device.
Figure 4:
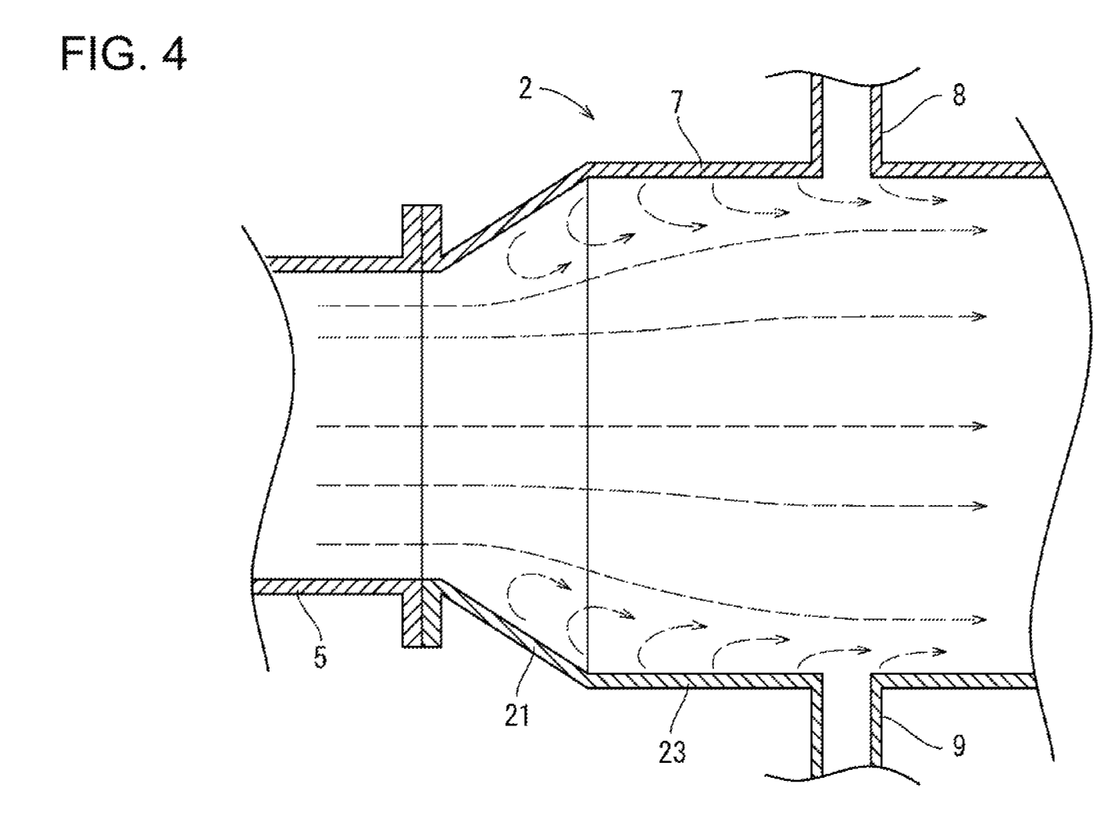
FIG. 4 An enlarged cross-sectional view of the measurement pipe.

FIG. 2 is a schematic diagram illustrating a system structure of the gas concentration measuring device of the present embodiment. FIG. 3 is a cross-sectional view illustrating the structure of the gas concentration measuring device of the present embodiment.

As shown in FIG. 1 to FIG. 3, the gas concentration measuring device 1 of the present embodiment includes: a measurement pipe (measurement cell) 2 through which sample gas containing target gas flows; a light emitter 3 configured to apply laser light to the measurement pipe 2; and a light receiver 4 configured to receive laser light transmitted through the measurement pipe 2. The measurement pipe 2 is provided between a gas supply pipe 5 and a gas discharge pipe 6. The sample gas is supplied from the gas supply pipe 5 to the measurement pipe 2 and flows into the gas discharge pipe 6 from the measurement pipe 2. That is, the gas supply pipe 5 is connected to an exhaust gas entrance side of the measurement pipe 2, while the gas discharge pipe 6 is connected to an exhaust gas exit side of the measurement pipe 2. Herein, when an element is referred to as being "connected to" another element, it can be directly connected to the other element or intervening elements may be present. As the sample gas, exhaust gas from a combustion system or fuel gas to a gas system is supplied, for example. Examples of target gas for measurement include ammonia, hydrogen halide, nitrogen oxides, sulfur oxides, carbon monoxide, carbon dioxide, oxygen, water, hydrocarbon, hydrogen sulfide, and the like. Concentration of such a gas species having a characteristic of absorbing infrared range light is measured.

The light emitter 3 and the light receiver 4 are provided so as to be symmetrical with the measurement pipe 2 interposed between them. An optical axis from the light emitter 3 to the light receiver 4 is orthogonal to a flow direction of the sample gas flowing through the measurement pipe 2. The measurement pipe 2 includes a main pipe 7 through which sample gas flows. At a side wall of the main pipe 7, an incoming pipe (branch pipe) 8 and an outgoing pipe (branch pipe) 9 are provided. The incoming pipe 8, through which laser light from the light emitter 3 is guided into the main pipe 7 of the measurement pipe 2, is provided so as to be opposed to the position where the light emitter 3 is provided. The outgoing pipe 9, through which laser light having been transmitted through the main pipe 7 is guided to the light receiver 4, is provided so as to be opposed to the position where the light receiver 4 is provided. In other words, the incoming pipe 8 and the outgoing pipe 9 are provided so that their longitudinal directions are along a radial direction of the main pipe 7 and so as to be symmetrical with respect to an axis of the main pipe 7.

The light emitter 3 includes a laser diode (not illustrated) configured to emit laser light. A laser light outgoing side of the light emitter 3 is connected to an incoming side of an optical axis adjuster 10 including an optical system configured to adjust the optical axis of emitted laser light. The outgoing side of the optical axis adjuster 10 is connected to the incoming pipe 8 of the measurement pipe 2 via a purge gas guide pipe 11 through which purge gas to be ejected to the optical axis adjuster 10 flows. That is, the light emitter 3 is connected to the incoming pipe 8 of the measurement pipe 2 via the optical axis adjuster 10 and via the purge gas guide pipe 11.

The light receiver 4 includes a photo diode (not illustrated) configured to receive laser light to perform photoelectric conversion. A laser light incoming side of the light receiver 4 is connected to an outgoing side of an optical axis adjuster 12 including an optical system configured to adjust the optical axis of incoming laser light. A light incoming side of the optical axis adjuster 12 is connected to the outgoing pipe 9 of the measurement pipe 2 via a purge gas guide pipe 13 through which purge gas to be ejected to the optical axis adjuster 12 flows. That is, the light receiver 4 is connected to the outgoing pipe 9 of the measurement pipe 2 via the optical axis adjuster 12 and via the purge gas guide pipe 13.

Purge gas such as instrument air and nitrogen gas is subjected to flow rate adjustment in a purge flow rate adjuster 16 connected to a purge gas source 15, and then through branching gas pipes 17, 18, purge gas is supplied into the purge gas guide pipes 11, 13 from gas inlets 19, 20, respectively. That is, the gas pipes 17, 18 respectively connect the gas inlets 19, 20 of the purge gas guide pipes 11, 13 to the purge flow rate adjuster 16.

Gas flowmeters 30, 31 are respectively provided on the gas pipes 17, 18. The gas flowmeters 30, 31 are configured to measure the flow rates of purge gas supplied to the purge gas guide pipes 11, 13, respectively, and to output signals indicating the measured flow rates to a measurement controller 32. The purge flow rate adjuster 16 is configured to adjust the flow rate of supplied purge gas based on a command signal from the measurement controller 32.

The measurement controller 32 is configured to set the flow rate of supplied purge gas based on a flow rate of sample gas flowing through the main pipe 7 of the measurement pipe 2, and to output a command signal to the purge flow rate adjuster 16 to notify the set flow rate. Meanwhile, the measurement controller 32 is configured to give a command signal to the light emitter 3, to cause the light emitter 3 to emit laser light having a wavelength corresponding to the absorption spectrum of the target gas (laser light in the near-infrared range), and to receive a measurement signal indicating the amount of laser light received by the light receiver 4. Upon reception of the measurement signal from the light receiver 4, the measurement controller 32 is configured to check the amount of transmitted light indicated by the measurement signal, and to calculate concentration of the target gas in the sample gas based on the above-described Equation (1) according to TDLAS technique. Furthermore, the measurement controller 32 is configured to detect a change of the flow rate of the sample gas, and to adjust the flow rate of purge gas depending on the detected change.

The measurement pipe 2 includes: a gas entrance portion 21 including an inlet through which the sample gas enters; a gas exit portion 22 including an outlet through which the sample gas is discharged; and a hollow tube-like measurement portion 23 provided between the gas entrance portion 21 and the gas exit portion 22. That is, the main pipe 7 is structured by the gas entrance portion 21, the gas exit portion 22, and the measurement portion 23. The incoming pipe 8 and the outgoing pipe 9 are provided so as to protrude from a side wall of the measurement portion 23.

The gas entrance portion 21 is connected to the gas supply pipe 5 and has a tapered shape such that its inner diameter increases toward the measurement portion 23. Meanwhile, the gas exit portion 22 is connected to the gas discharge pipe 6 and has a tapered shape such that its inner diameter increases toward the measurement portion 23. As for the main pipe 7 of the measurement pipe 2, the inner diameter of the measurement portion 23 is larger than the inner diameter of the inlet of the gas entrance portion 21 and than the inner diameter of the outlet of the gas exit portion 22. The main pipe 7 is shaped to taper narrower like bottlenecks toward its both ends respectively connected to the gas supply pipe 5 and the gas discharge pipe 6. That is, the inner diameter of the measurement portion 23, in which measurement is performed in the measurement pipe 2, is larger than the inner diameter of the gas supply pipe 5 and than the inner diameter of the gas discharge pipe 6. The measurement pipe 2 has the gas entrance portion 21 shaped so as to taper narrower toward its end (having a frustum like shape) so that its cross-sectional area decreases toward an upstream side in a flow direction of the sample gas, and this suppresses or reduces the entry of the sample gas into the incoming pipe 8 and the outgoing pipe 9 in the measurement portion 23.

As shown in FIG. 3, an inner diameter R2 of the measurement portion 23 is larger than an inner diameter R1 of the inlet of the gas entrance portion 21. Due to this, the sample gas tends to flow through a central portion of the measurement portion 23, and the width of the flow of the sample gas widens from the gas entrance portion 21 toward a downstream side. Here, the incoming pipe 8 and the outgoing pipe 9 are provided upstream of a position where the sample gas flow width reaches an inner wall of the measurement portion 23. This reduces the amount of the sample gas entering the incoming pipe 8 and the outgoing pipe 9 and makes the sample gas flow width constant at the position where the incoming pipe 8 and the outgoing pipe 9 are provided.

Because the entry of the sample gas into the incoming pipe 8 and the outgoing pipe 9 can be suppressed or reduced, it is possible to decrease the flow rate of purge gas supplied to the purge gas guide pipes 11, 13 to a smaller rate. Upon reception of a measurement signal indicating a flow rate Sf of the sample gas flowing through the gas supply pipe 5, the measurement controller 32 is configured to set a flow rate Pf of supplied purge gas based on the following Equation (2):

$$Pf=(K1 \times Sf)/(R2^2/R1^2)^2$$

(where K1 represents a constant.)

As described above, the gas concentration measuring device 1 of the present embodiment includes the light emitter 3 and the light receiver 4 which are provided so as to be opposed to each other with the hollow tube-like measurement pipe 2 interposed therebetween, and the device 1 is configured to measure concentration of target gas passing through the measurement pipe 2 using light applied from the light emitter 3, transmitted through the inside of the measurement pipe 2, and received by the light receiver 4. The purge gas guide pipes 11, 13 through which purge gas is introduced into the optical systems of the light emitter 3 and the light receiver 4 are connected to the side wall of the measurement pipe 2. The measurement pipe 2 includes the gas entrance portion 21 having a tapered shape widening from a gas supply port toward the downstream side. The purge gas guide pipes 11, 13 are disposed at positions downstream of the gas entrance portion 21 so as to be opposed to each other and so as to be orthogonal to the flow direction of the sample gas (to a longitudinal direction of the measurement pipe 2).

With this arrangement, the entry of the sample gas into connecting portions between the purge gas guide pipes 11, 13 and the measurement pipe 2 can be suppressed or reduced in the measurement pipe 2. Therefore, the optical path length of laser light applied to the sample gas in the measurement pipe 2 can be maintained constant, to improve the reliability of measured gas concentration values. In addition, it is possible to suppress or reduce the flow rate of purge gas supplied to the purge gas guide pipes 11, 13. This can lead to not only downsizing of devices for supplying purge gas but also reduction of power or fuel cost for driving such devices.

The measurement portion 23 of the measurement pipe 2, which is connected to the purge gas guide pipes 11, 13, has a hollow tube-like shape having an inner diameter equal to a maximum inner diameter of the gas entrance portion 21. Furthermore, the gas exit portion 22, which is at a downstream end portion of the measurement pipe 2, has a tapered shape widening toward the upstream side from a gas discharge port. In other words, the gas exit portion 22 provided downstream of the measurement portion 23 has a tapered shape narrowing toward the gas discharge port of the downstream end portion. That is, the measurement pipe 2 is shaped to taper narrower toward its both ends like bottlenecks.

The flow rate of the purge gas supplied to the purge gas guide pipes 11, 13 is calculated based on: the ratio of the cross-sectional area of the measurement portion 23, functioning as a longer-diameter portion, to the cross-sectional area of a gas inlet port, functioning as a shorter-diameter portion; and the flow rate of the sample gas flowing through the measurement portion 23. Here, the larger the ratio of the cross-sectional area of the longer-diameter portion of the measurement pipe 2 to the cross-sectional area of the shorter-diameter portion of the measurement pipe 2, the better the entry of the sample gas into the purge gas guide pipes 11, 13 is suppressed or reduced. Thus, the flow rate of purge gas can be calculated easily and can be properly set depending on the flow rate of the sample gas.

The structure of each component is not limited to the illustrated embodiment, but can be variously changed within the scope and spirit of the present invention. For example, the device may be configured so that purge gas is supplied to each of the incoming pipe 8 and the outgoing pipe 9 of the measurement pipe 2, without providing the purge gas guide pipes 11, 13. While in the above-described embodiment, the measurement portion 23 of the measurement pipe 2 has a cylindrical or circular hollow tube-like shape, the shape of the measurement portion 23 is not limited to this. The measurement portion 23 may have a polygonal hollow tube-like shape, for example.

REFERENCE SIGNS LIST 1 gas concentration measuring device
2 measurement pipe (measurement cell)
3 light emitter
4 light receiver
5 gas supply pipe
6 gas discharge pipe
7 main pipe
8 incoming pipe (branch pipe)
9 outgoing pipe (branch pipe)
10 optical axis adjuster
11 purge gas guide pipe
12 optical axis adjuster
13 purge gas guide pipe
15 purge gas source
16 purge flow rate adjuster
17 gas pipe
18 gas pipe
19 gas inlet
20 gas inlet
21 gas entrance portion
22 gas exit portion
23 measurement portion
30 gas flowmeter
31 gas flowmeter
32 measurement controller

The invention claimed is:

1. A gas concentration measuring device comprising:
a measurement pipe defining a channel and including:
    a gas entrance portion having a tapered shape widening from a gas supply port toward a downstream side in a flow direction of a gas; and
    a hollow measurement portion having a constant inner diameter and provided downstream of the gas entrance portion in the flow direction of the gas;
    purge gas guide pipes connected to a side wall of the measurement pipe and provided to the measurement portion, each of the purge gas guide pipes configured to introduce purge gas into the measurement pipe, the purge gas guide pipes positioned such that a first purge gas guide pipe and a second purge gas guide pipe of the purge gas guide pipes are opposed to each other and oriented orthogonal to a longitudinal direction of the measurement pipe;
    a light emitter coupled to the measurement pipe and configured to emit light; and
    a light receiver coupled to the measurement pipe and configured to receive at least a portion of the light via the channel, the light receiver and the light emitter disposed on opposing sides of the measurement pipe, and
wherein the light emitter and the light receiver are configured to measure concentration of the gas passing through the measurement pipe; and
    a controller configured to calculate a flow rate of purge gas supplied to the purge gas guide pipes based on:
    a ratio determined based on a first value associated with a cross-sectional area of the measurement portion and a second value associated with a cross-sectional area of a gas port of the measurement pipe; and
    a flow rate of gas entering the measurement pipe.

2. The gas concentration measuring device according to claim 1, wherein:
    the measurement pipe further includes a gas exit portion provided downstream of the measurement portion; and
    the gas exit portion has a tapered shape narrowing toward a gas discharge port of a downstream end portion of the measurement pipe in the flow direction of the gas.

3. The gas concentration measuring device according to claim 1, wherein the controller is further configured to:
    detect a change of the flow rate of the gas entering the measurement pipe; and
    adjust the flow rate of purge gas depending on the detected change.

4. The gas concentration measuring device according to claim 1, further comprising:
    a gas discharge pipe coupled to an outlet of the measurement pipe; and
    a gas supply pipe coupled to an inlet of the measurement pipe.

5. A gas concentration measuring system, comprising:
    a pipe comprising:
        an inlet;
        an outlet; and
        a sidewall that defines a channel configured to convey a first gas in a flow direction from the inlet to the outlet;
    at least one guide pipe coupled to the sidewall, the at least one guide pipe in fluid communication with the pipe and configured to introduce purge gas into the channel;
    a light system coupled to the pipe, the light system comprising:
        a light emitter configured to transmit a light though the channel along an optical axis; and
        a light receiver configured to receive the light transmitted by the light emitter; and
    a controller in communication with the light system, the controller configured to:
        calculate a flow rate of purge gas supplied to the at least one guide pipe based on:
        a maximum diameter of the channel;
        a diameter of the channel at the inlet or the outlet; and
        a flow rate of the first gas flowing through the pipe;
        determine a gas concentration of the first gas;
        detect a change of the flow rate of the first gas flowing through the pipe, and
        based on the change of the flow rate of the first gas, adjust the flow rate of the purge gas supplied to the at least one guide pipe.

6. The gas concentration measuring system of claim 5, further comprising:
    a purge flow rate adjuster coupled to the controller; and wherein the controller is further configured to:
transmit a signal to the purge flow rate adjuster to adjust the flow rate of purge gas.

7. The gas concentration measuring system of claim 5, wherein the controller is configured to:
transmit a wavelength signal to the light emitter to emit laser light having a wavelength corresponding to an absorption spectrum of a target gas; and
receive a measurement signal indicating an amount of laser light received by the light receiver.

8. The gas concentration measuring system of claim 7, wherein the controller is configured to, based on the measurement signal:
determine the amount of laser light indicated by the measurement signal; and
calculate a concentration of the target gas in the first gas.

9. The gas concentration measuring system of claim 5, wherein:
the controller is configured to:
calculate a first cross-sectional area of the channel based on the maximum diameter of the channel;
calculate a second cross-sectional area of the channel based on the diameter of the channel at the inlet or the outlet; and
calculate the flow rate of the purge gas supplied to the at least one guide pipe further based on the first cross-sectional area and the second cross-sectional area.

10. The gas concentration measuring system of claim 9, wherein the pipe further comprises:
a measurement portion;
a gas entrance portion extending from the inlet to the measurement portion, the gas entrance portion being tapered; and
a gas exit portion extending from the measurement portion to the outlet, the gas entrance portion being tapered; and
wherein the first cross-sectional area of the pipe is located in the measurement portion.

11. The gas concentration measuring system of claim 10, wherein:
the at least one guide pipe comprises:
a first guide pipe coupled to the sidewall; and
a second guide pipe coupled to the sidewall, the second guide pipe coupled to the pipe at a location opposing the first guide pipe such that the channel is interposed between the first and second guide pipes;
the light emitter is coupled to the first guide pipe; and
the light receiver is coupled to the second guide pipe.

12. The gas concentration measuring system of claim 11, wherein first and second guide pipe extending radially away from the sidewall along the optical axis.

13. The gas concentration measuring system of claim 5, wherein the optical axis is orthogonal to the flow direction.

14. The gas concentration measuring system of claim 13, further comprising:
a gas discharge pipe coupled to the outlet of the pipe; and
a gas supply pipe coupled to the inlet of the pipe.

15. The gas concentration measuring system of claim 5, further comprising a purge gas source configured to introduce purge gas through the at least one guide pipe.

16. The gas concentration measuring system of claim 15, further comprising one or more gas flowmeters coupled to the purge gas source and configured to measure the flow rate of purge gas supplied to the at least one guide pipe.

17. A gas concentration measuring system, comprising:
a controller configured to:
receive, from a gas flowmeter, a flow rate of a first gas flowing through a channel of a pipe;
calculate a first flow rate of purge gas to be supplied to the channel of the pipe via one or more guide pipes;
transmit, to a purge flow rate adjuster, a first signal configured to set a flow rate of purge gas to the first flow rate;
transmit, to a light system comprising a light emitter and a light receiver, a second signal configured to cause the light emitter to emit laser light having a wavelength corresponding to an absorption spectrum of a target gas; and
receive, from the light system, a measurement signal indicating an amount of laser light received by the light receiver;
calculate a concentration of the target gas in the first gas;
receive, from the gas flowmeter, a change signal indicating a change of the flow rate of the first gas; and
based on the change signal:
calculate a changed flow rate of the purge gas based on:
a ratio based on a first cross-sectional area of the channel and a second cross-sectional area of the channel at an inlet port or an outlet port of the channel, the first cross-sectional area larger than the second cross-sectional area; and
the flow rate of the first gas.

18. The gas concentration measuring system of claim 17, wherein the controller is further configured to:
transmit, to the purge flow rate adjuster, a second signal configured to adjust a flow rate of purge gas to the changed flow rate.

* * * * *